(12) United States Patent
Johnson et al.

(10) Patent No.: US 7,201,770 B2
(45) Date of Patent: Apr. 10, 2007

(54) EVERTING BALLOON STENT DELIVERY SYSTEM HAVING TAPERED LEADING EDGE

(75) Inventors: Kirk L. Johnson, Weston, FL (US); Stephen J. Querns, deceased, late of Hayesville, NC (US); by Melissa Querns, legal representative, Hayesville, NC (US)

(73) Assignee: Cordis Corporation, Miami Lakes, FL (US)

( * ) Notice: Subject to any disclaimer, the term of this patent is extended or adjusted under 35 U.S.C. 154(b) by 633 days.

(21) Appl. No.: 10/281,659

(22) Filed: Oct. 28, 2002

(65) Prior Publication Data

US 2003/0105508 A1 Jun. 5, 2003

Related U.S. Application Data

(63) Continuation-in-part of application No. 09/532,353, filed on Mar. 21, 2000, now abandoned.

(51) Int. Cl.
*A61F 2/06* (2006.01)

(52) U.S. Cl. .................................... 623/1.12

(58) Field of Classification Search ............... 606/108; 623/1.12, 1.11, 1.23
See application file for complete search history.

(56) References Cited

U.S. PATENT DOCUMENTS

| | | |
|---|---|---|
| 3,911,927 A | 10/1975 | Rich et al. |
| 4,271,839 A | 6/1981 | Fogarty et al. |
| 4,479,497 A | 10/1984 | Fogarty et al. |
| 4,530,698 A | 7/1985 | Goldstein et al. |

(Continued)

FOREIGN PATENT DOCUMENTS

EP 0 366 478 B1 5/1990

(Continued)

*Primary Examiner*—Michael Thaler
(74) *Attorney, Agent, or Firm*—Michael W. Montgomery (57) ABSTRACT

A stent delivery catheter includes at least an inner and outer body, and a specially shaped balloon affixed near one end of both of the inner and outer bodies. At least the outer body is tubular, and the space between the outer and inner bodies defines an inflation lumen for inflating and deflating the balloon. The balloon is designed to surround and hold a compressed self-expanding stent in a small initial size. An inner portion of the cylindrical balloon extends from where it is affixed to the inner body of the catheter shaft at a point proximal to the stent to a distal leading edge at a point distal to the stent. At this leading edge, the balloon is folded back upon itself, and an outer portion of the balloon extends proximally from the leading edge to a point proximal of the stent where it is affixed to the outer body of the catheter shaft. When the outer body is retracted in the proximal direction, the balloon progressively peels back or everts, to progressively release the stent. This peeling action minimizes any friction that may exist between the stent and balloon during stent deployment. The leading distal folded edge of the balloon, both inner and outer portions, are tapered inward. This inner and outer tapering of the balloon portions tends to protect the leading edge of the stent, provides for easier advancement of the catheter system along the desired body passageway for treatment, and minimizes friction as the balloon is retracted or peeled back upon itself.

9 Claims, 10 Drawing Sheets

U.S. PATENT DOCUMENTS

| | | |
|---|---|---|
| 4,606,347 A | 8/1986 | Fogarty et al. |
| 4,655,771 A | 4/1987 | Wallsten |
| 4,771,765 A | 9/1988 | Choy et al. |
| 4,820,270 A | 4/1989 | Hardcastle et al. |
| 4,848,343 A | 7/1989 | Wallstén et al. |
| 4,863,440 A | 9/1989 | Chin |
| 4,954,126 A | 9/1990 | Wallstén |
| 4,990,151 A | 2/1991 | Wallstén |
| 5,061,275 A | 10/1991 | Wallstén et al. |
| 5,074,845 A | 12/1991 | Miraki et al. |
| 5,163,927 A | 11/1992 | Woker et al. |
| 5,171,305 A | 12/1992 | Schickling et al. |
| 5,286,254 A | 2/1994 | Shapland et al. |
| 5,300,023 A | 4/1994 | Lowery et al. |
| 5,346,498 A | 9/1994 | Greelis et al. |
| 5,347,247 A | 9/1994 | Gruchalla |
| 5,374,247 A | 12/1994 | Lowery et al. |
| 5,383,889 A | 1/1995 | Warner et al. |
| 5,389,089 A | 2/1995 | Bauer et al. |
| 5,458,573 A | 10/1995 | Summers |
| 5,514,093 A | 5/1996 | Ellis et al. |
| 5,549,551 A | 8/1996 | Peacock, III et al. |
| 5,630,797 A | 5/1997 | Diedrich et al. |
| 6,039,721 A | 3/2000 | Johnson et al. |

FOREIGN PATENT DOCUMENTS

| | | |
|---|---|---|
| EP | 0 541 258 B1 | 5/1993 |

EVERTING BALLOON STENT DELIVERY SYSTEM HAVING TAPERED LEADING EDGE

CROSS-REFERENCE TO RELATED APPLICATION

The present invention is a continuation-in-part of U.S. patent application Ser. No. 09/532,353, filed on Mar. 21, 2000 now abandoned.

BACKGROUND AND SUMMARY OF THE INVENTION

1. Introduction

This invention relates to medical devices, and more particularly to catheters for delivering medical devices.

2. Discussion

Stents are a type of medical device that has been used with great success to treat various conditions of patients, including narrowing or blockage of a blood vessel or other body passage. Generally, stents are often formed as cylindrical mesh tubes which expand from an initial configuration to a deployed shape. In the deployed shape, they act as scaffolding to hold open a body passage or lumen, such as an artery.

Stents have so far been provided in two broad categories, balloon-expandable and self-expanding. Balloon-expandable stents are crimped around a deflated balloon of a balloon catheter, delivered to a desired site for treatment, and forcibly expanded by inflating the balloon to a certain pressure to the deployed shape.

On the other hand, self-expanding stents are compressed to a small initial size and then surrounded by a tube or sheath. Accordingly, self-expanding stent delivery systems do not need a balloon of any kind, resulting in a system fewer components. Once the self-expanding stent is positioned within a desired site for treatment where it is to be implanted, the sheath is withdrawn slightly and pulled from around the stent, while at the same time the stent is held in the desired position. When the stent is uncovered, it tends to automatically and resiliently expand to the desired deployed shape.

With such an arrangement, there may be some amount of initial friction between the sheath and the stent that may occur during stent deployment. Also, a stent that has greater length may tend to generate greater friction.

Accordingly, it is an object of the present invention to provide a delivery system for self-expanding stents which minimizes friction during deployment of the stent.

In addition, it is possible to provide stents with one or more coatings. Such coatings may be of various types, including medicated or therapeutic coatings, lubricious coatings, etc. Of course, it is also desirable to minimize even a remote possibility of damage to a coating during deployment of a coated stent.

An example embodiment of a catheter made according to the principles of the present invention includes a long flexible shaft, a proximal hub assembly, and a specially shaped balloon.

The shaft has an inner body and an outer body. At least the outer body is tubular and surrounds at least a portion of the inner body. The inner body may be tubular as well, and if so, it defines a guidewire lumen.

The term "tubular" is used in its broadest sense; to encompass any structure arranged a radial distance around a longitudinal axis. Accordingly, tubular includes any structure that (i) is cylindrical or not, such as for example an elliptical or polygonal cross-section, or any other regular or irregular cross-section; (ii) has a different or changing cross-section along its length; (iii) is arranged arowid a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; (vi) has any desired combination of length or cross-sectional size.

The relative positions of the inner and outer bodies can be adjusted by moving them axially or longitudinally with respect to each other.

The balloon is generally cylindrical, and includes an inner and outer balloon portion. The inner and outer balloon portions are affixed to the inner and outer shaft bodies respectively. The area where they are joined is called the inner and outer proximal shoulder of the balloon, respectively. The inner and outer balloon portions extend distally from these proximal shoulders, and meet at a distal leading edge fold. The entire balloon surrounds a stent in an initial configuration, compressing the stent and holding it in place.

According to the unique arrangement of the present invention, the distal area of the balloon has a novel shape, in that the distal section of both the inner and outer balloon portions are both tapered inward. This feature tends to protect the leading distal end of the stent, and also provides for easier advancement of the catheter system along the desired passage for treatment.

The outer hub defines an inflation port connected to the inner tube. An adjustable seal is interposed between the outer hub and the inner body tube. When tightened, the seal secures the inner body tube in a selected position relative to the outer body tube. When the seal is adjusted to a release position, the inner body tube and the outer body tube lumen tube may be moved axially relatively to adjust the effective length of the balloon between its retracted and extended positions. Indicia on the guide wire tube indicate to the physician the relative spacing of the balloon inner and outer shoulders.

Where the stent is surrounded by a deflated balloon, the balloon is advanced into the vessel to be treated until it is within a stenosis to be treated. The inner body tube is then held stationary while the outer body tube is withdrawn to peel the balloon from the stent. Thus, the balloon will be peeled gradually from the stent from the distal to the proximal end of the stent, and allowing the stent to expand and thereby become implanted at a desired location.

Thereafter, if desired, the catheter is may be moved a short distance to position the balloon within the stent, and the balloon may be inflated to assure full stent expansion. The catheter is then removed from the patient being treated.

Accordingly, an object of the present invention is to provide a novel and improved balloon catheter stent delivery system, and processes of utilizing such a catheter for expanding stenoses, opening occlusions, as well as protecting and implanting stents to diseased vessel wall segments.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
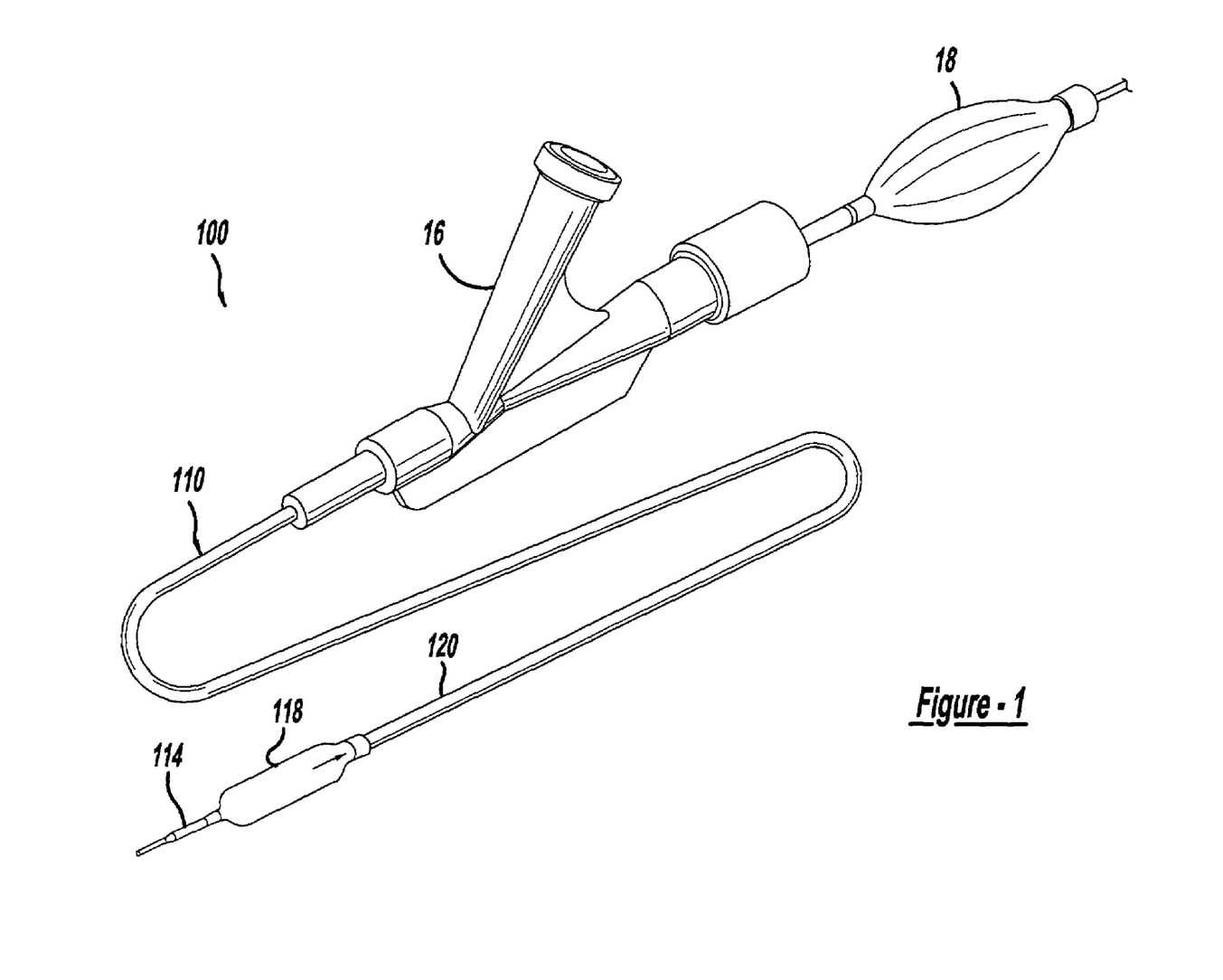
FIG. 1 is a perspective view of a balloon catheter and medical device delivery system, arranged according to the principles of this invention.
Figure 2:
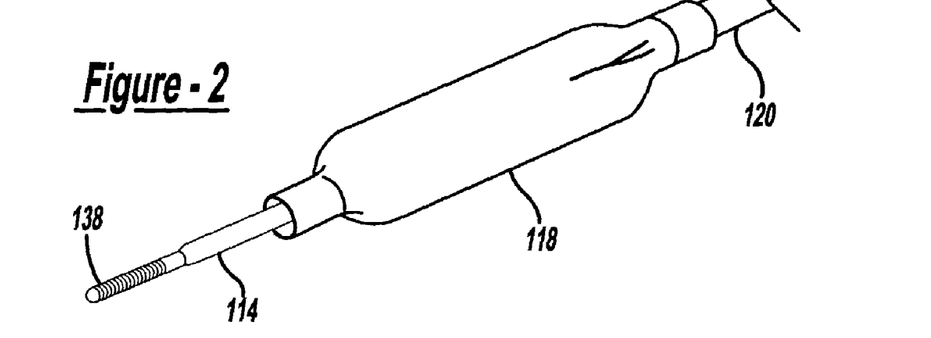
FIGS. 2 and 3 are partial perspective views of selected embodiments of the present invention.
Figure 3:
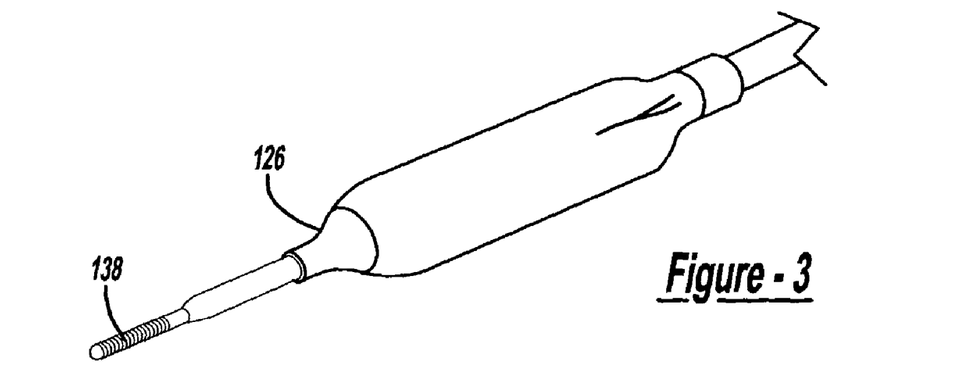

Referring to the drawings and to FIGS. 1 and 2 in particular, one embodiment of a catheter is shown generally at 10. The catheter 10 utilizes the usual guide wire 138. A flexible shaft inner body tube 114 surrounds the guide wire 138. In use, inner body 114 is slidable longitudinally on the guide wire for insertion into and withdrawal from a blood vessel or other body passage of a patient being treated.

An elongate cylindrical outer body tube 120 is concentrically disposed about the inner body 114. A proximal outer hub 16 is fixed to the proximal end of the outer body 120, and a proximal inner hub 18 is fixed to the proximal end of the inner body 114.

The outer hub 16 also includes an inflation/deflation port communicating with an inflation lumen, defined by an annular space between the inner and outer bodies 114 and 120. The outer hub 16 carries an annular seal which circumscribes the inner body 114. An annular thumbscrew is threaded into outer hub 16 for controllably compressing the seal to effect a fluid tight seal between the outer hub and the inner body 114. The inner body 114 has a plurality of position-indicating indicia near its proximal end. The indicia function to indicate to a physician the relative longitudinal spacing of the distal ends of the inner and outer bodies 114 and 120.

An annular balloon 118 is also provided near the distal end of the catheter. The balloon 26 has an outer shoulder attached to the outer body 120, and an inner shoulder attached to the inner body 114. The balloon has an outer portion 124 extending distally from the outer shoulder of the balloon to a folded leading edge, and an inner portion 122 extending proximally from the folded leading edge to the inner shoulder. Because the entire balloon is annular or cylindrical, the folded leading edge describes a circle.

According to the novel configuration of the present invention, the distal most area of both the inner and outer portions 122 and 124 of the balloon 118 are tapered radially inward. This "double taper" design may tend to reduce friction as the balloon is peeled back to deploy the stent, and may tend to protect the stent as well as resisting the balloon from uncovering the stent, including during movement of the entire system. The tapered portions of the inner and outer portions 122 and 124 are shown for example in FIG. 4. The tapers are exaggerated for clarity, in that the minimum diameter of the inner balloon portion 122 should not interfere with the sent 112.

When the outer hub 16 is retracted, the balloon and double tapers gently peel back to uncover and deploy the stent. Most of the catheter system, including the balloon and inner and outer bodies are made of flexible, though substantially inelastic, material. Accordingly, the double taper and folded leading edge of the balloon may be provided with a slight interference fit, without inhibiting release of the stent.

Figure 4:
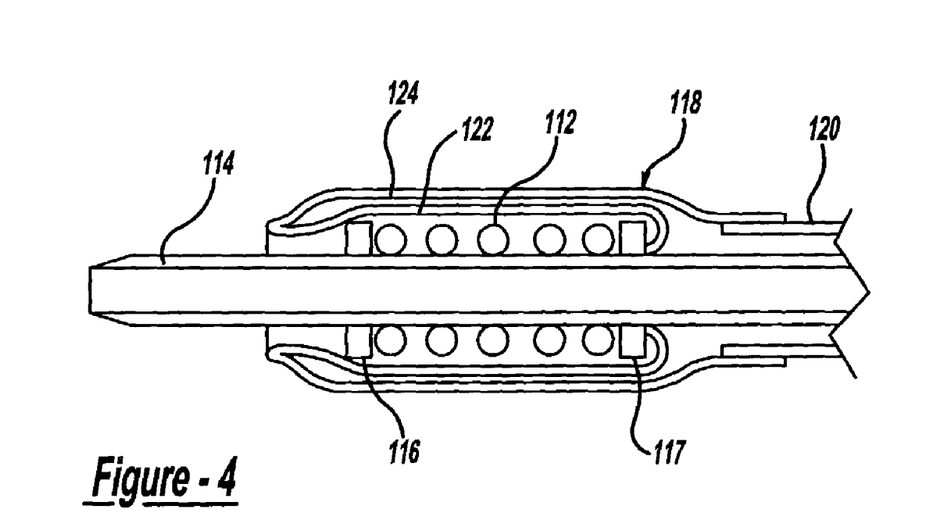
FIGS. 4 and 8 are partial cross-section views of embodiments of FIGS. 2 and 3, respectively.
Figure 5:
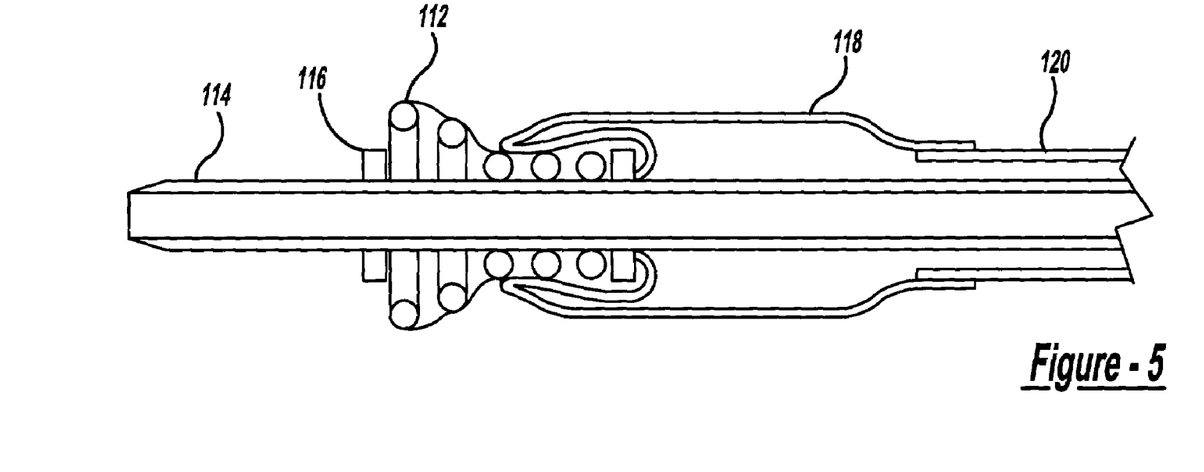
FIGS. 5 and 6 are sequential partial cross-section views showing implantation of a stent with the catheter of FIGS. 2 and 4.
Figure 6:
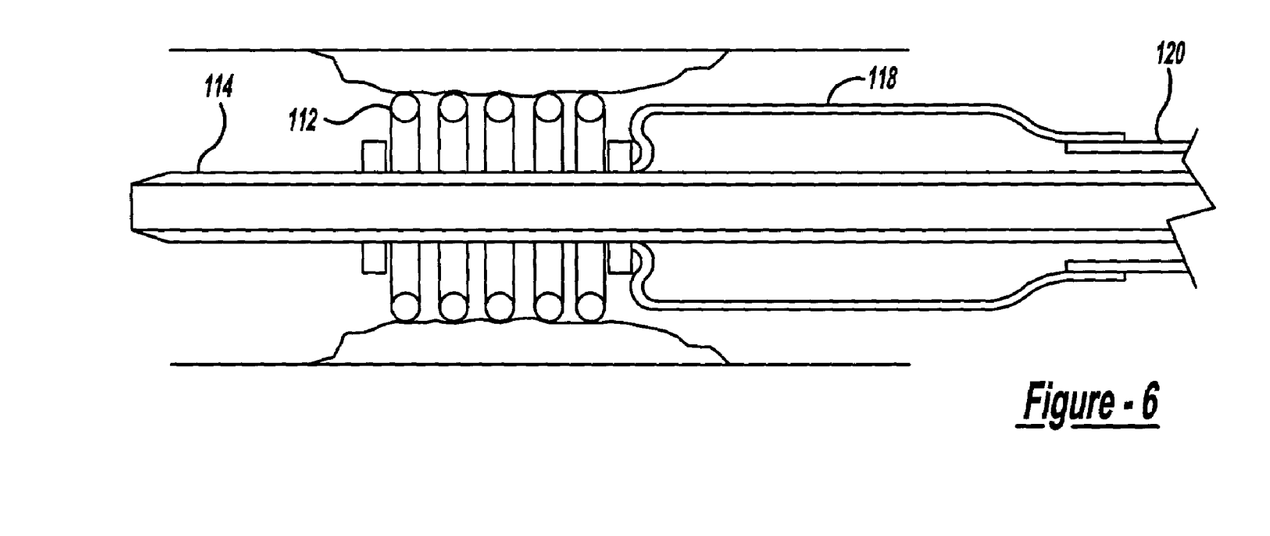

As indicated by a comparison of FIGS. 4–6, the outer body 120 is relatively moveable, when the seal is released, between an initial position as shown in FIG. 4 and a retracted position as shown in FIG. 6. Thus, the balloon 118 is adjustable between the position of FIG. 4 where the balloon is folded on itself, and the position of FIG. 6 where the balloon 118 is fully retracted. The effect of this adjustment is to gently and gradually deploy the stent, with substantially no friction on the stent 112 itself.

Preparation

The balloon 118 is preferably made of any suitable thermoplastic material, which can be thermally treated to take on a slight "set" in a desired or initial position. This optional thermoset process can be conducted by choosing a high temperature sterilization process, such as for example using ethylene oxide gas at elevated temperatures. If desired, an effect of this sterilization procedure is that the thermoplastic material of which the balloon 118 may be made is temporarily set in its initial compressed and deflated condition through the heat of sterilization. In practice, balloons are made of a variety of thermoplastic materials, including nylon, PET and polyethylene. For the present disclosure nylon is the preferred material.

Stent Implantation

Referring now to FIGS. 4–7, a self-expanding stent 112 is shown in a compressed condition in FIG. 4. For illustrative purposes FIGS. 4–7 show the stent being positioned within a stenosis 36 in a blood vessel 35.

Prior to insertion of the catheter 100 to implant the stent 112, the stent is placed over the inner body 114. The catheter is adjusted to position the balloon in its initial position of FIG. 4. The stent is compressed to a diameter small enough to position it within the balloon 118 and around the distal end of the inner body 114. When so positioned, the balloon functions to constrain the stent 112 in its compressed condition. Preferably the balloon is fully deflated to the point where the balloon is longitudinally folded on itself to provide inner and outer portions or layers 122 and 124 circumscribing and constraining the stent.

After the stent has been compressed and positioned within the balloon, the catheter is inserted until the stent is located within the lesion or stenosis 36. When the catheter 10 is to be used to treat a patient, the thumbscrew on the outer hub 16 is loosened, and the outer body 120 is retracted relative to the inner body 114. Once the balloon is appropriately positioned, the seal in the outer hub 16 is relaxed to the extent necessary to permit relative axial movement of the tubes 114 and 120 as illustrated in FIGS. 5 and 6. The outer body 120 is then retracted, as the inner body 114 is maintained stationary to resist retractive motion of the stent. The retraction of the outer body 120 is continued to "peel" the balloon from the stent, allowing it to expand to the position of FIG. 7. The balloon may later be positioned within the stent and inflated to fully expand or "tack" the stent in place, if warranted by a particular case. Thereafter the catheter is withdrawn.

Referring now to FIGS. 1, 2 and 4–6, a self-expanding stent 112 is shown in a compressed condition in FIG. 4. Prior to insertion of the catheter 110 to implant the stent 112, the stent is placed over inner body tube 114, between flanking stops or marker bands 116 and 117. The catheter is initially adjusted to position a balloon 118 in its retracted position of FIGS. 1, 2 and 4. The stent 112 is compressed to a diameter small enough to position it within the annular balloon 118, and between the distal ends of inner body tube 114 and outer body tube 120. When so positioned, the balloon 118 functions to constrain the stent 112 in its compressed condition. Preferably, the balloon is folded on itself, to provide inner and outer layers 122 and 124 circumscribing and constraining the stent. Both of the inner and outer portions or layers 122 and 124 of the balloon 118 of FIGS. 1, 2 and 4–6 are also preferably tapered at their distal ends. In other words, the folded balloon has two overlapping portions 122 and 124 which collectively taper at their distal ends for easier introduction and advancement of the catheter system along the vasculature.

Figure 7:
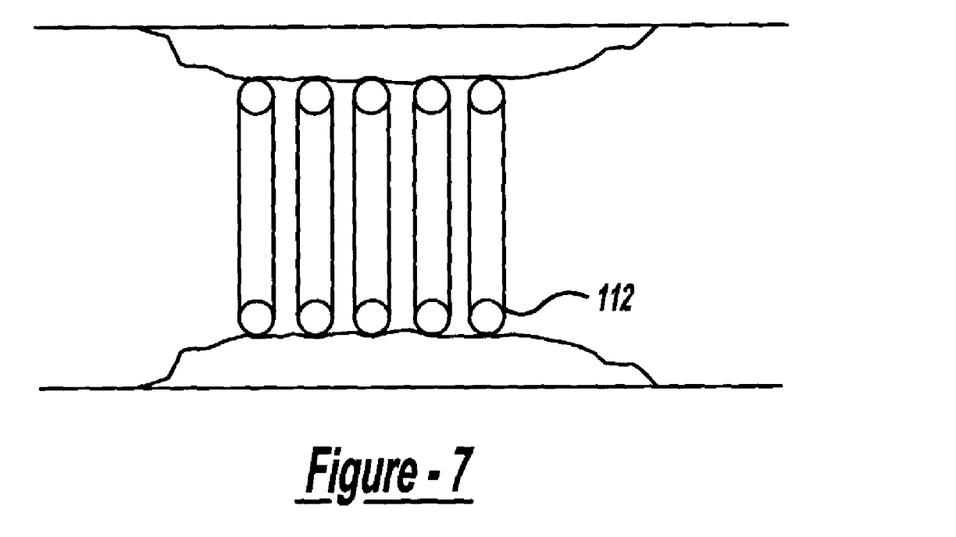
FIG. 7 depicts a cross-section view of a stent deployed within a lesion of a body passage.
Figure 8:
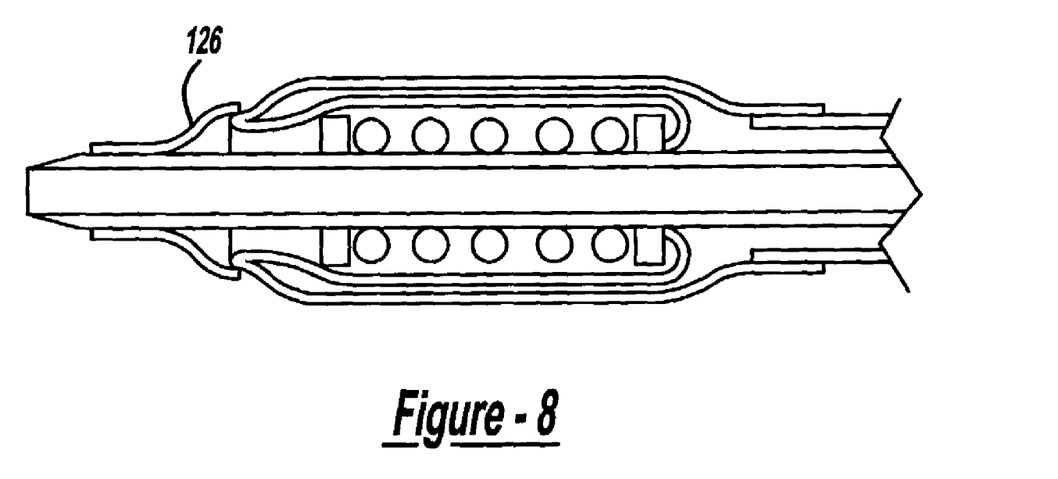

Operation of the system is shown in FIGS. 4–6. The catheter system 100 is introduced in the configuration of FIG. 4 until the stent is within a desired site for treatment. Then, outer body 120 is withdrawn in the proximal direction while inner body 114 is held in place, causing the folded balloon to evert and peel back to release the stent, as shown in FIGS. 5 and 6. The deployed stent is depicted in FIG. 7.

Figure 9:
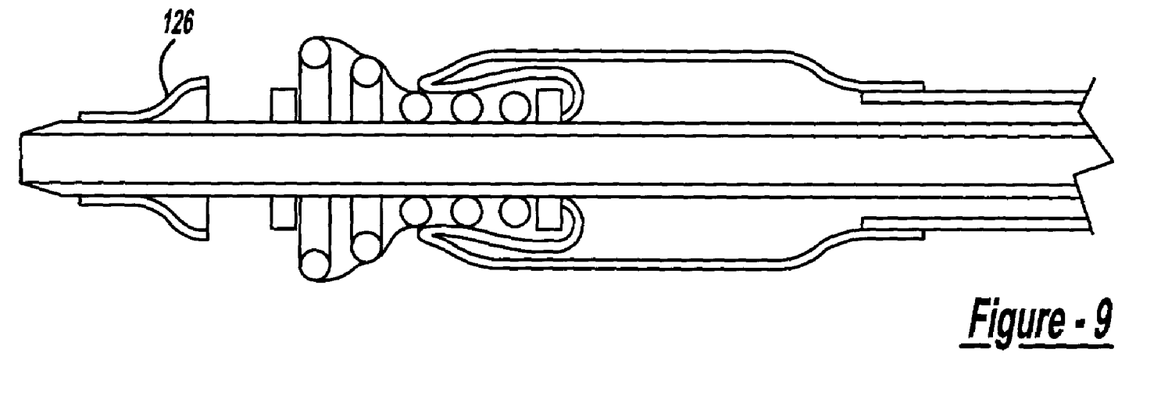
FIGS. 9 and 10 are sequential partial cross-section views showing implantation of a stent with the catheter of FIGS. 3 and 8.
Figure 10:
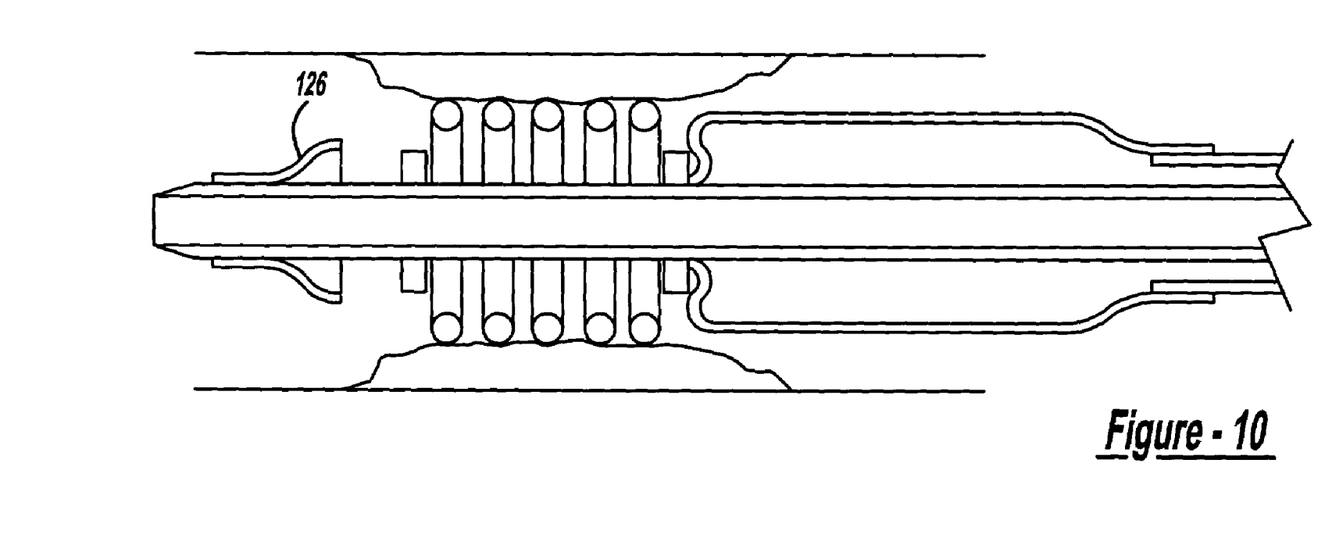

Another embodiment of the present invention is shown in FIGS. 3 and 8–10, which is similar to the stent delivery catheter depicted in FIGS. 2 and 4–6 with the addition of a leading edge transition member 126, which further assists easy introduction and advancement of the catheter system. Operation is similar to FIGS. 5 and 6, and is shown in FIGS. 9 and 10.

Figure 11:
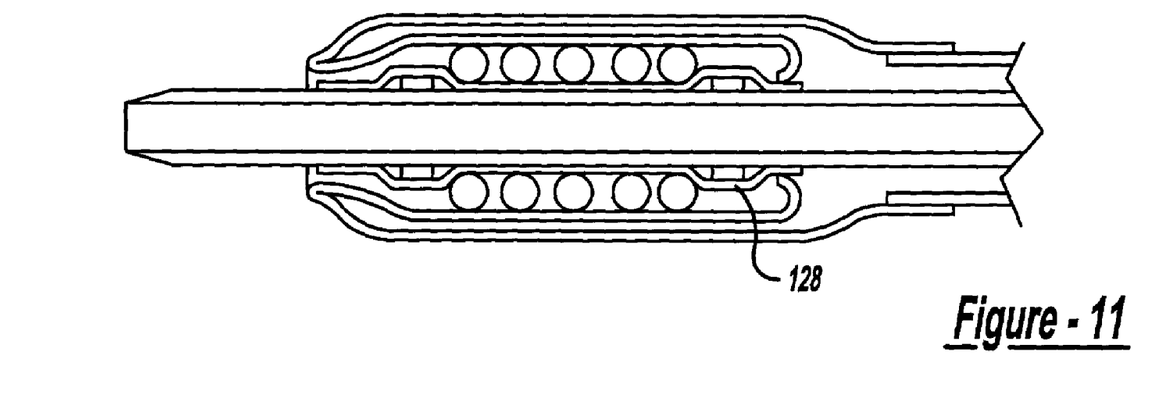
FIGS. 11 and 14 are partial cross-section views of additional embodiments of the present invention.
Figure 12:
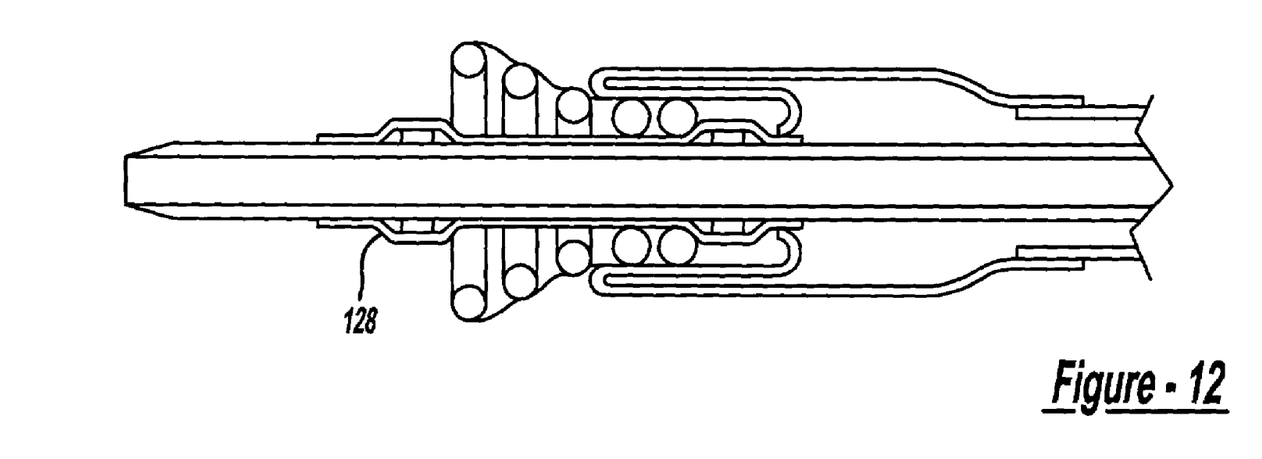
FIGS. 12 and 13 are sequential partial cross-section views showing implantation of a stent with the catheter of FIG. 11.
Figure 13:
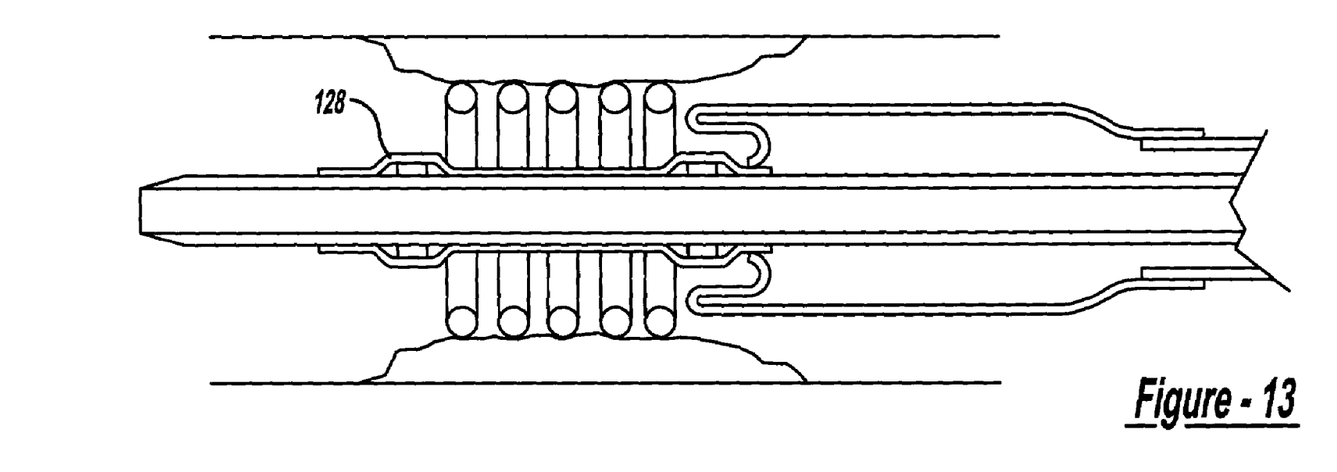

Another embodiment of the present invention is shown in FIGS. 11–13, which is similar to the stent delivery catheter depicted in FIGS. 2 and 4–6 with the addition of an inner sleeve 128, which protects the interface between the stent 112 and marker bands 116.

Figure 14:
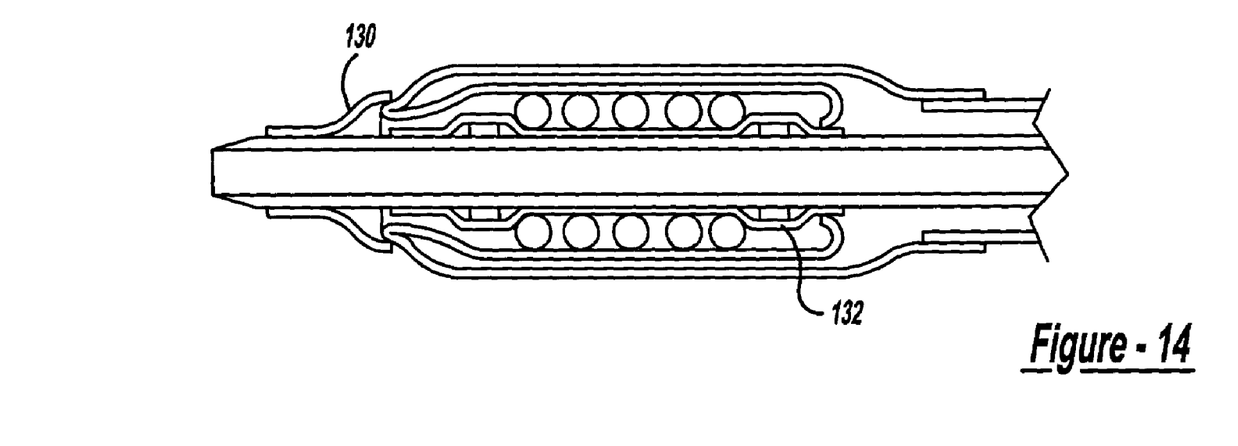
Figure 15:
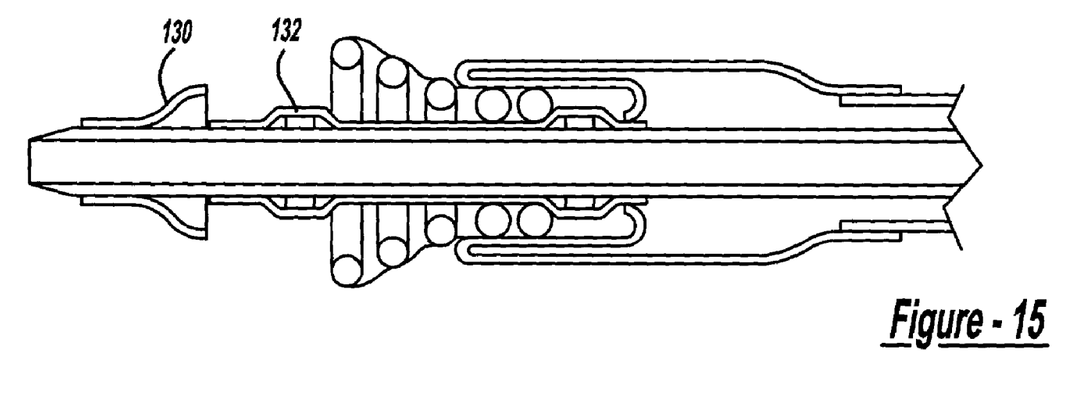
FIGS. 15 and 16 are sequential partial cross-section views showing implantation of a stent with the catheter of FIG. 14.
Figure 16:
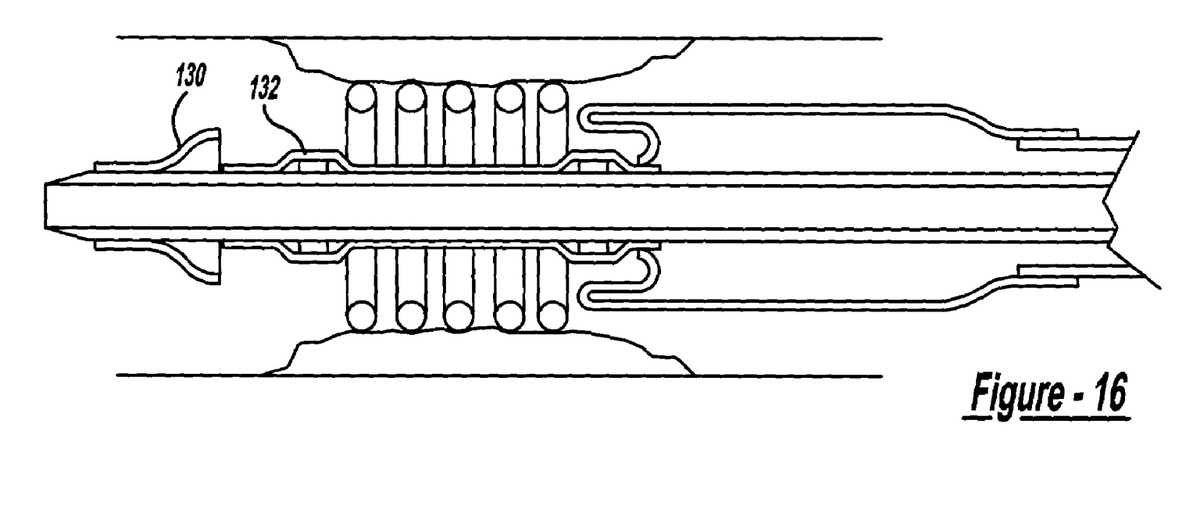

FIGS. 14–16 shows a stent delivery catheter system combining the added features of a leading edge transition member 130 and an inner protective sleeve 132.

Figure 18:
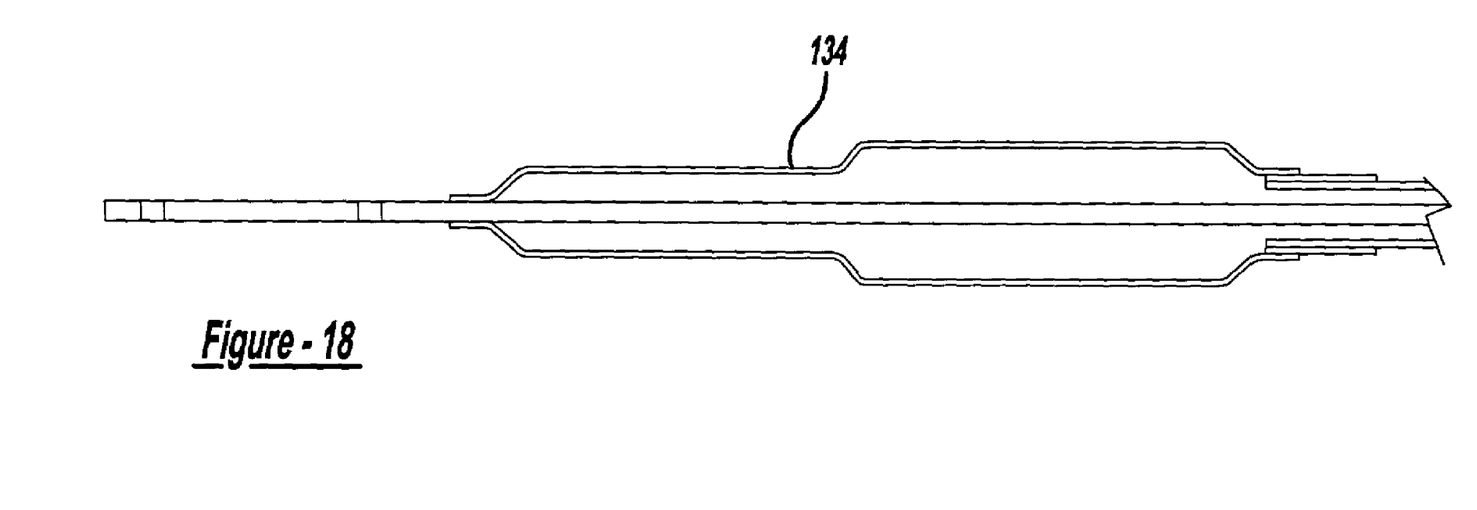
Figure 19:
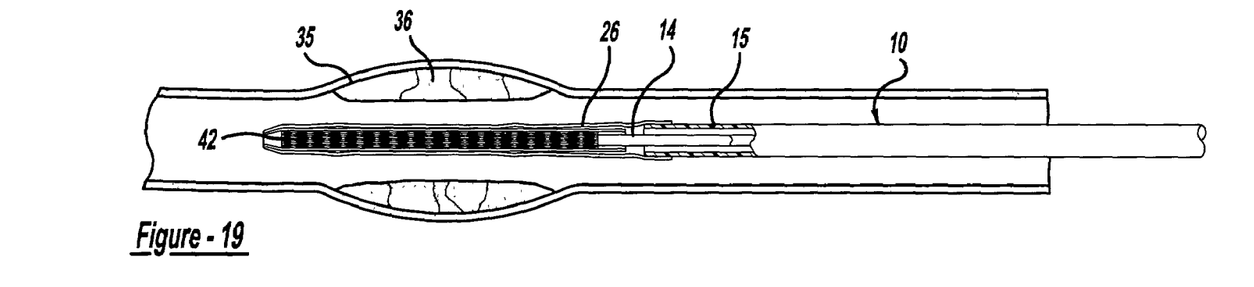
FIG. 19 is a partial cross-section view of yet another embodiment of the present invention.
Figure 20:
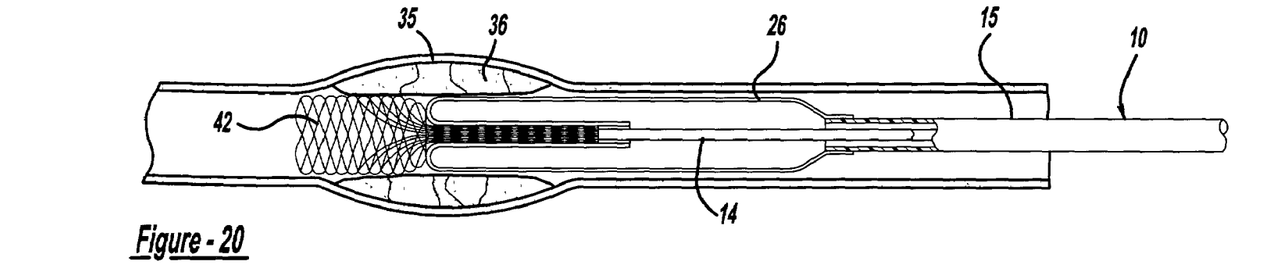
FIGS. 20 and 21 are sequential partial cross-section views showing implantation of a stent with the catheter of FIG. 19.
Figure 21:
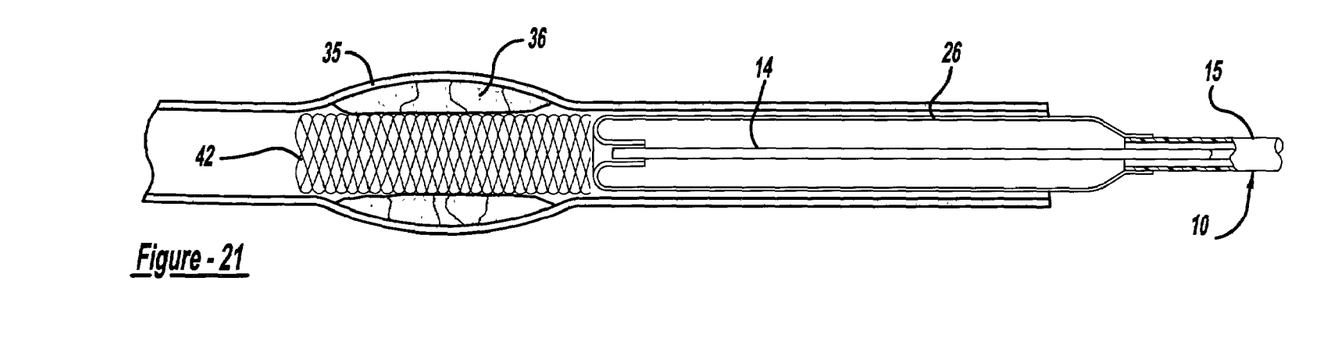

The stent delivery catheter system of this present invention preferably has an everted balloon for initially compressing and holding the stent, which can be progressively rolled back to deliver the stent as shown in FIGS. 19–21 and other drawings. FIG. 18 shows a fully everted balloon 134. In an initial configuration, the everted balloon preferably has a tapered leading edge at its distal end. This tapered leading edge minimizes contact friction between the layers of the inverted balloon, as the tapered leading edge will tend to constrain the crimped stent at a smaller diameter than the untapered trailing edge will tend to constrain the crimped stent at a smaller diameter than the untapered trailing edge, creating a gap between the layers of the inverted balloon.

Figure 17:
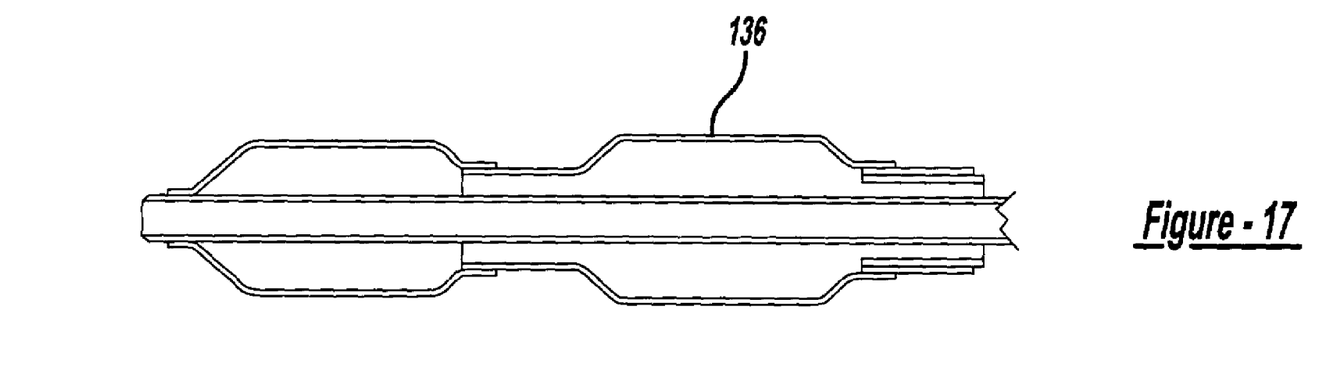
FIGS. 17 and 18 are each partial cross-section views of possible arrangements of balloons according to the principles of the present invention, in selected configurations.

One way to provide such a tapered leading edge is to shape the balloon with a waist or narrowing, whether the balloon 136 is made with a single piece or more than one piece, as shown in FIG. 17.

FIGS. 19–21 show another embodiment of a catheter 10 which includes an outer body tube 15 concentrically disposed about an inner body 14. An annular balloon 26 is provided at the distal end of the catheter, for delivering a stent 42 within a lesion or stenosis 36 of a body passage 35.

Although the invention has been described in its preferred form with a certain degree of particularity, it is understood that the present disclosure of the preferred form has been made only by way of example and that numerous changes in the details of construction, operation and the combination and arrangement of parts may be resorted to without departing from the spirit and the scope of the invention as hereinafter claimed.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A stent delivery system, comprising:
   a catheter shaft defining a longitudinal axis having a proximal and distal end, including a flexible inner body and a flexible tubular outer body at least partially surrounding the inner body, a space between the inner and outer bodies defining an inflation lumen;
   a cylindrical polymer balloon affixed to the catheter shaft near the shaft distal end, the inflation lumen communicating with an interior of the balloon; the balloon having an outer shoulder attached to the outer body and an inner shoulder attached to the inner body, the balloon having an outer portion extending distally from the outer shoulder to a folded leading edge, and having an inner portion extending proximally from the folded leading edge to the inner shoulder;
   a tubular stent having a compressed initial size and an expanded size, the stent tending to resiliently expand from the compressed to the expanded size; wherein the stent is initially compressed and mounted within the balloon; such that in an initial configuration the inner and outer portions of the balloon surround the stent and hold it to the initial compressed size;
   both of the inner and outer portions of the balloon taper radially inward toward said longitudinal axis in a distal direction near the distal folded leading edge of the balloon, such that an inner and outer balloon taper tend to facilitate advancement of the stent delivery system to the desired site for treatment;
   the outer body is moveable with respect to the inner body; when the outer body is retracted in the proximal direction, the balloon progressively peels back to reveal and release to stent; wherein the inner and outer taper tend to reduce friction between the inner and outer balloon portions when the balloon is progressively peeled back.

2. The stout delivery system of claim 1, further comprising a guidewire lumen defined by and extending through at least a portion of the inner body.

3. The stent delivery system of claim 1, further comprising a leading edge transition ramp member attached to and surrounding the inner body near a distal end of the inner body, defining an angled surface extending annularly from a point near the distal end of the inner body radially outward to an area near the distal leading edge fold of the balloon, the ramp member having generally a cone shape.

4. The stent delivery system of claim 1, wherein the distal end of the inner body is distal of the stent, such that the inner body provides structural support within the entire length of the stent.

5. The stent delivery system of claim 1, further comprising a pair of marker bands attached to the inner body in positions flanking the stent.

6. The stent delivery system of claim 5, further comprising a sleeve surrounding the inner body and marker bands; the sleeve extending from a point proximal to the proximal marker band to a point distal to the distal marker band, and tending to protect the stent from contact with one or both marker bands.

7. The stern delivery system of claim 1, wherein the inner body is tubular and defines a guidewire lumen extending from a distal guidewire port near the inner body distal end to a proximal guidewire port.

8. The stent delivery system of claim 7, wherein the proximal guidewire port is positioned in a proximal hub attached to a proximal end of the outer body, in an over-the-wire configuration.

9. The stent delivery system of claim 1, wherein the leading folded edge of the balloon is distal of the distal ends of both the inner and outer bodies in the initial configuration, and the stent is also distal of the inner and outer bodies while it is within the balloon.

* * * * *